United States Patent [19]
Nantz et al.

[11] Patent Number: 6,043,390
[45] Date of Patent: Mar. 28, 2000

[54] PENTAERYTHRITOL LIPID DERIVATIVES AND NUCLEIC-ACID COMPLEXES

[75] Inventors: Michael H. Nantz, Davis; Alfred M. Aberle, Vallejo, both of Calif.

[73] Assignee: The Regents of the University of California, Oakland, Calif.

[21] Appl. No.: 09/055,021

[22] Filed: Apr. 3, 1998

[51] Int. Cl.[7] ..................... C07C 229/04; C07C 229/24; C07C 229/26
[52] U.S. Cl. .................... 560/169; 560/171; 560/224; 560/156
[58] Field of Search ................... 560/224, 156, 560/169, 171

[56] References Cited

U.S. PATENT DOCUMENTS

| | | | |
|---|---|---|---|
| 4,529,561 | 7/1985 | Hunt et al. | 264/4.3 |
| 4,737,323 | 4/1988 | Martin et al. | 264/4.3 |
| 5,264,618 | 11/1993 | Felgner et al. | 560/224 |
| 5,334,761 | 8/1994 | Gebeyehu et al. | 564/197 |
| 5,527,928 | 6/1996 | Nantz et al. | 554/105 |

OTHER PUBLICATIONS

Szoka & Papahadjopoulos, "Procedure for preparation of liposomes with large internal aqueous space and high cap ture by reverse–phase evaporation," Proc. Natl. Acad. Sci. USA, 75(9):4194–4198 (Sep. 1978).

Bloomfield, "Quasi–elastic light scattering applications in biochemistry and biology," Ann. Rev. Biophys. Bioeng., 10:421–450 (1981).

Gruenert., et al., "Long–term culture of normal and cystic fibrosis epithelial cells grown under serum–free conditions," In Vitro Cell Dev. Biol., 26:411–418 (Apr. 1990).

Stribling, et al., "Aerosol gene delivery in vivo," Proc. Natl. Acad. Sci. USA, 89:11277–11281 (Dec. 1992).

Zhu, et al., "Systemic gene expression after intravenous DNA delivery into adult mice," Science, 261:209–211 (1993).

Aberle, Alfred M., et al., "A novel tetraester construct that reduces cationic lipid–associated cytotoxicity. Implications for the onsent of cytotoxicity," *Biochemistry,* 37:6533–6540 (1998).

*Primary Examiner*—Floyd D. Higel
*Attorney, Agent, or Firm*—Townsend and Townsend and Crew LLP

[57] ABSTRACT

This invention relates to pentaerythritol lipid derivatives which are useful for the intracellular delivery of polynucleotides. These cationic lipids are useful in the preparation of liposomes and other lipid vesicles for the delivery of nucleic acids into mammalian cells.

6 Claims, 3 Drawing Sheets

PENTAERYTHRITOL LIPID DERIVATIVES AND NUCLEIC-ACID COMPLEXES

FIELD OF THE INVENTION

This invention relates to pentaerythritol lipid derivatives which are useful for the intracellular delivery of polynucleotides. These cationic lipids are useful in the preparation of liposomes and other lipid vesicles for the delivery of nucleic acids into mammalian cells.

BACKGROUND OF THE INVENTION

The introduction of foreign nucleic acids and other molecules is a valuable method for manipulating cells and has great potential both in molecular biology and in clinical medicine. Many methods have been used for insertion of endogenous nucleic acids into eukaryotic cells. Genetic material can be introduced into cells to express an encoded protein which is deficient or defective. The use of such technology allows for the treatment of genetic based diseases. Gene transfer entails distributing nucleic acids to target cells and then transferring the nucleic acid across a target cell membrane in a form that can function in a therapeutic manner. Of the many methods used to facilitate entry of DNA into eukaryotic cells, cationic liposomes are among the most efficacious and have found extensive use as DNA carriers in transfection experiments. Cationic lipids themselves are known to bind to polynucleotides and to facilitate their intracellular delivery into mammalian cells. Nucleic acid is negatively charged and when combined with a positively charged lipid forms a complex that is suitable for formulation and cellular delivery. The use of cationic lipid carriers for transfection is well established. However, their ability to mediate transfection is not well understood.

The precise way in which nucleic acids and cationic lipids interact and the structure formed before and during the transfection process are not well known. It is commonly believed that the nucleic acids are entrapped within a lipid bilayer, which is the classic definition of a "liposome." There is also a belief, however, that the nucleic acid does not become entrapped, but forms some other sort of aggregate with the cationic lipids. It has also been reported that liposome-DNA aggregate size and shape are a function of the ratio of the amount of DNA to that of cationic lipid. It has been concluded that DNA binds to the outer surface of liposomes, which then cluster into irregular spherical aggregates. Plasmid length had no effect on binding to liposomes and the structure of the liposome-DNA complex is believed to change at charge neutrality, while the DNA becomes organized into a very compact structure that is evidently quite different from a liposome. It has been concluded that the liposome probably uses at least two pathways to introduce DNA into cells: fusion with the plasma membrane and endocytosis.

The delivery and expression of a transfected gene constitute a complex process that includes steps involving transfection complex (lipoplex) formulation, cellular internalization, endosomal escape, and nuclear localization. Incorporation of cationic lipid in the cytoplasmic membrane can occur by cytoplasmic fusion or translocation after lipoplex uptake. Incorporation of the cationic lipid in the cytoplasmic membrane can occur by cytoplasmic fusion or translocation after lipoplex uptake. Cellular processes can be inhibited by the incorporation of positively charged lipids into the plasma membrane. This incorporation can lead to cell dysfunction and possibly cell death. Thus, although there are benefits to cationic lipid facilitated gene transfer, there are also deleterious effects of lipidic salts on cellular processes. The long-term administration of cationic lipoplexes has been shown to elicit inflammatory responses and cytotoxicity.

Lipid-associated cytotoxicity has been attributed to the inhibition of protein kinase C activity by cationic lipids after internalization of the lipoplex. This is presumably a consequence of cationic lipid incorporation into the plasma membrane. In addition, transfection is attributed to the formation of transmembrane pores. There are also resultant disruptions of signal transduction and gene regulation processes which impair cellular function. It is possible that enhanced clearance of the cationic lipids might alleviate the cytotoxicity.

There exists a need to design lipids which are effective in facilitating intracellular delivery of genetic material, but that will reduce the associated cellular toxicity. The present invention fulfills this and other needs.

SUMMARY OF THE INVENTION

In one aspect, the present invention relates to an amphiphilic lipid for the intracellular delivery of polynucleotides having Formula I

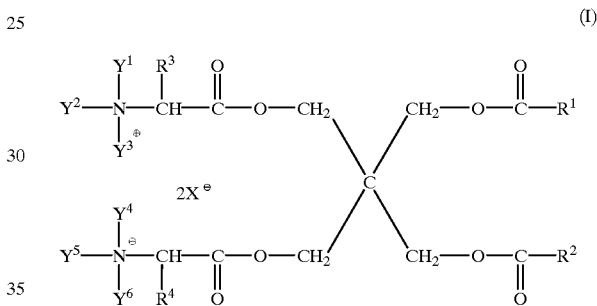

In Formula I, $R^1$ is a functional group including, but not limited to, $C_8$–$C_{24}$ alkyl and $C_8$–$C_{24}$ alkenyl. The alkenyl groups may have more than one site of unsaturation and the double bonds may be cis or trans. $R^2$, in Formula I, is a functional group including, but not limited to, $C_8$–$C_{24}$ alkyl and $C_8$–$C_{24}$ alkenyl. The alkenyl groups may have more than one site of unsaturation and the double bonds may be cis or trans. $R^3$, in Formula I, is a functional group including, but not limited to, hydrogen, optionally substituted $C_1$–$C_8$ alkyl, optionally substituted arylalkyl, $C_1$–$C_8$ alkylthioalkyl, guanidinoalkyl, carboxyalkyl, aminoalkyl, carbamoyl $C_1$–$C_8$ alkyl and heteroarylalkyl. $R^4$, in Formula I, is a functional group including, but not limited to, hydrogen, optionally substituted $C_1$–$C_8$ alkyl, optionally substituted arylalkyl, $C_1$–$C_8$ alkylthioalkyl, guanidinoalkyl, carboxyalkyl, aminoalkyl, carbamoyl $C_1$–$C_8$ alkyl and heteroarylalkyl. $Y^1$, in Formula I, is a functional group including, but not limited to, hydrogen and $C_1$–$C_6$ alkyl. $Y^2$, in Formula I, is a functional group including, but not limited to, hydrogen and $C_1$–$C_6$ alkyl. $Y^3$, in Formula I, is a functional group including, but not limited to, hydrogen and $C_1$–$C_6$ alkyl. $Y^4$, in Formula I, is a functional group including, but not limited to, hydrogen and $C_1$–$C_6$ alkyl. $Y^5$, in Formula I, is a functional group including, but not limited to, hydrogen and $C_1$–$C_6$ alkyl. $Y^6$, in Formula I, is a functional group including, but not limited to, hydrogen and $C_1$–$C_6$ alkyl. X, in Formula I, is an anion, such as a halogen, including chloride, iodide, fluoride and bromide or an oxyanion. In an alternative embodiment, $R^3$, $Y^1$ and the atoms to which they are bound, join to form an optionally substituted 5- or 6-membered heterocyclic ring. In an alternative embodiment, $R^4$, $Y^6$ and the atoms to which they are bound, join to form an optionally substituted 5- or 6-membered heterocyclic ring.

The cationic lipids of Formula I are attractive for a number of reasons. These novel cationic lipids are derived from pentaerythritol which provides a unique "linchpin" framework that differs from current diacylpropanaminium motifs commonly used in gene transfer. Furthermore, the lipids of Formula I are less toxic than known cationic lipids, due in part to their amino acid metabolic by-products. In addition, the liposomes and lipid complexes whose lipids include the cationic lipids of Formula I have been shown to have comparable transfection efficiencies to the cationic lipids of the prior art.

In another aspect, this invention relates to a lipid-nucleic acid complex, the lipid portion of which contains an amphiphilic cationic lipid of Formula I.

In yet another aspect, this invention relates to a method for transfecting a nucleic acid into a cell. In this method, the cell is contacted with a lipid-nucleic acid complex, or liposome, the lipid portion of which contains an amphiphilic cationic lipid of Formula I. Using standard techniques, the lipids of Formula I can facilitate the transfection of nucleic acids into cells, in vivo and in vitro, with high efficiency.

In still yet another aspect, this invention relates to a pharmaceutical composition or other drug delivery composition for administering a nucleic acid particle to a cell. This composition includes a lipid-nuclei acid complex, the lipid portion of which contains an amphiphilic cationic lipid of Formula I, and a pharmaceutically acceptable carrier.

In yet another aspect of the invention comprises novel methods of treating diseases arising from infection by a pathogen or from an endogenous DNA deficiency. These methods involve administering a liposome-nucleic acid aggregate and/or liposome-drug aggregate solution to a mammal suffering from a pathogenic infection or DNA deficiency.

GLOSSARY

Figure 1:
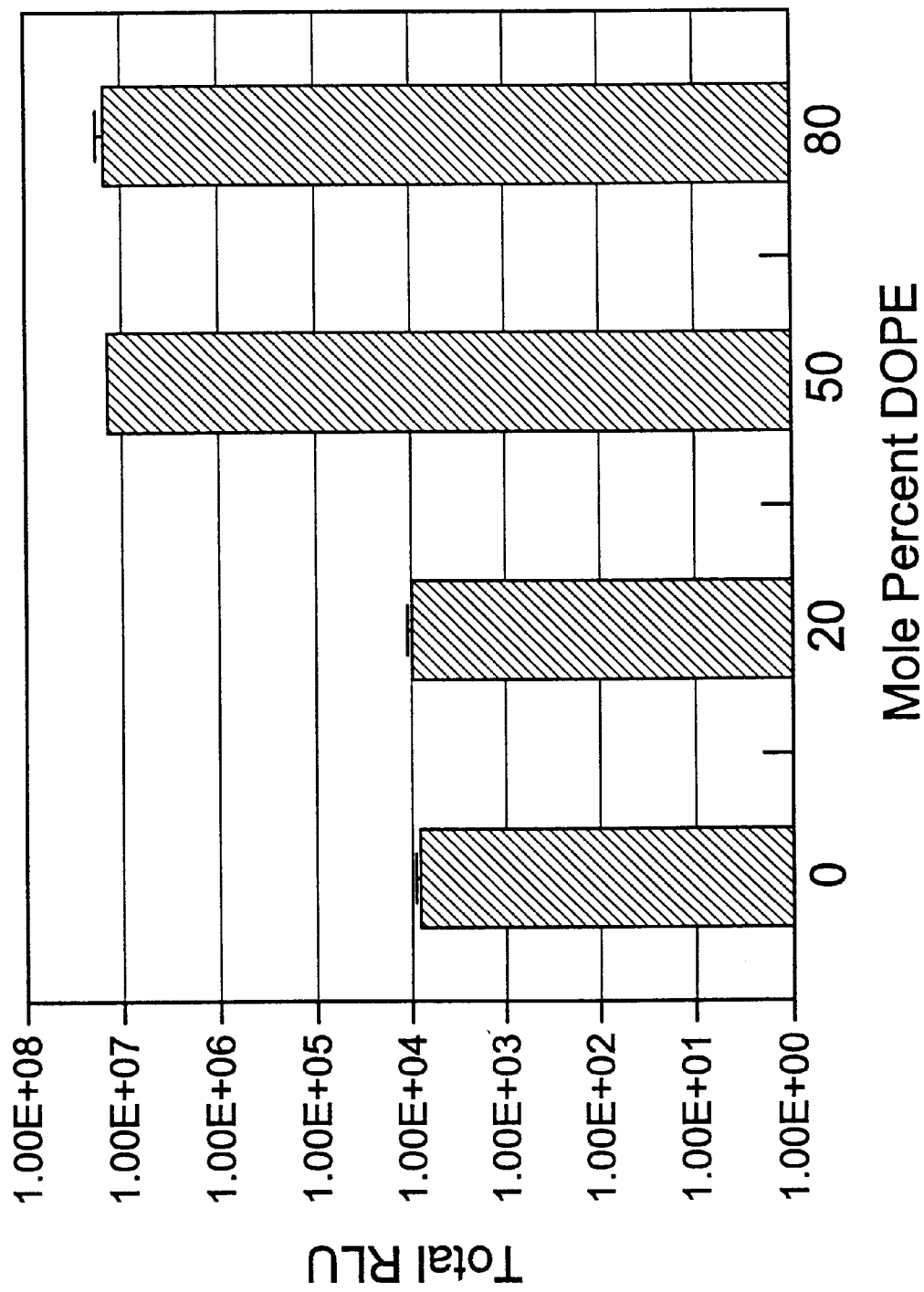
FIG. 1 is a bar graph showing the transfection activity of DMTM(Gly):DOPE liposomes as a function of the mole percent DOPE. DNA transfections were performed using NIH 3T3 cells. Lipoplexes were formulated at a 2:1 molar charge ratio (lipid charge to DNA phosphate charge). The values shown are the mean (n=4) and standard deviation of total luciferase light units (RLU) obtained from cells lysed after administration of 1 mg DNA.

The term "cationic lipid" refers to any of a number of lipid species which carry a net positive charge at physiological pH. Such lipids include, but are not limited to, dimyristoyl bis(N,N,N-trimethylglycyl) tetraester ("DMTM(Gly)"); dioleoyl bis (N,N,N-trimethylglycyl) tetraester ("DOTM(Gly)"); N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3β-(N-(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y., USA); LIPOFECTAMINE® (commercially available cationic liposomes comprising N-(1-(2,3-dioleyloxy)propyl)-N-(2-(sperminecarboxamido) ethyl)-N,N-dimethylammonium trifluoroacetate ("DOSPA") and ("DOPE"), from GIBCO/BRL); and TRANS-FECTAM® (commercially available cationic lipids comprising dioctadecylamidoglycyl carboxyspermine ("DOGS") in ethanol from Promega Corp., Madison, Wis., USA).

The term "lipid aggregate" denotes liposomes both unilamellar and multilamellar as well as micelles and virosomes and more amorphous aggregates of cationic lipids or lipids mixed with amphipathic lipids such as phospholipids.

As used herein, the term "alkyl" denotes branched or unbranched hydrocarbon chains, such as, methyl, ethyl, n-propyl, iso-propyl, n-butyl, sec-butyl, iso-butyl, tertbutyl, octa-decyl and 2-methylpentyl. These groups are optionally substituted with one or more functional groups which are attached commonly to such chains, such as, hydroxyl, bromo, fluoro, chloro, iodo, mercapto, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "alkenyl" denotes branched or unbranched hydrocarbon chains containing one or more carbon-carbon double bonds.

The term "aryl" denotes a chain of carbon atoms which form at least one aromatic ring having preferably between about 6–14 carbon atoms, such as phenyl, anthryl, naphthyl, indenyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl, propionyl, or butyryl.

The term "alkoxy" denotes —OR—, wherein R is alkyl.

The term "amino" denotes an amine linkage: —NR—, wherein R is hydrogen or alkyl.

The term "carboxylates" indicates —C(O)O—.

The term "oxyanions" indicates a general term for functional groups having an oxygen containing a negative charge, such as, aromatic or aliphatic carboxylates, sulfonates and sulfates.

The term "sulfonates" indicates R—S(O)$_2$O— wherein R can be aromatic or aliphatic.

The term "sulfates" indicates —RO—S(O)$_2$O— wherein R can be aromatic or aliphatic.

The term "side chain" of amino acids denotes the R group bonded to the α-carbon of naturally-occurring amino acids as well as synthetic amino acids and/or amino acid mimetics. This group includes both D- and L-amino acids. This group includes, but is not limited to, hydrogen (glycine); methyl (alanine); isopropyl (valine); iso-butyl (leucine); sec-butyl (isoleucine); hydroxymethyl (serine); benzyl (phenylalanine); 3-indolemethyl (tryptophan); pyrrolidine (proline); 4-hydroxypyrrolidine (hydroxy proline); 2-methylthioethyl (methionine); carboxymethyl (aspartate); carbamoylmethyl (asparagine); carboxyethyl (glutamic acid); carbamoylethyl (glutamine); aminobutyl (lysine); guanidinopropyl (arginine); imidazolylmethyl (histidine); 1-hydroxyethyl (threonine); hydroxyphenylmethyl (tyrosine) and thiomethyl (cyteine).

Examples of "synthetic amino acids" include norleucine, norvaline, alloisoleucine, homoarginine, thioproline, dehydroproline, hydroxyproline, isonipecotic acid, homoserine, cyclohexylglycine, α-amino-n-butyric acid, cyclohexylalanine, aminophenylbutyric acid, phenylalanines substituted at the ortho, meta, or para position of the phenyl moiety with one or two of the following: a (C$_1$–C$_4$) alkyl, a (C$_1$–C$_4$) alkoxy, halogen or nitro groups or substituted with a methylenedioxy group; β-2- and 3-thienylalalanine, β-2- and 3-furanylalanine, β-2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3- and 5-sulfo tyrosine, 3- and 5-carboxytyrosine, 3- and 5-phosphotyrosine, 4-methane sulfonic acid ester of tyrosine, 4-methane phosphonic acid ester of tyrosine, 4-phenylacetic acid, 3,5-diiodotyrosine, 3- and 5-ntirotyrosine, ε-alkyl lysine and, delta-alkyl ornithine.

DETAILED DESCRIPTION OF THE INVENTION AND PREFERRED EMBODIMENTS

A. Compound and Synthesis

The present invention relates to an amphiphilic lipid for the intracellular delivery of polynucleotides having Formula I

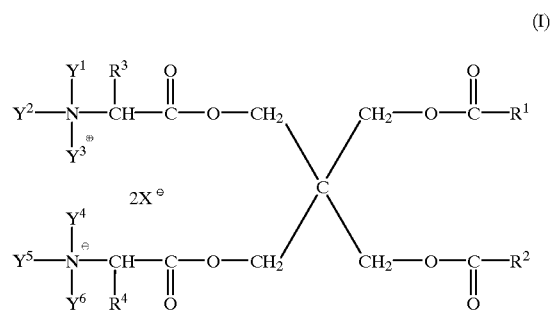

wherein, R$^1$, R$^2$, R$^3$, R$^4$, Y$^1$, Y$^2$, Y$^3$, Y$^4$, Y$^5$, Y$^6$ and X are as defined above. The amphiphilic cationic lipids of Formula I can be prepared by treatment of commercially available pentaerythritol with two equivalents of the appropriate acyl chloride. The acyl chlorides are commercially available or may be synthesized by using the desired fatty acid and oxalyl chloride under reaction conditions well known by those skilled in chemical synthesis.

The acylation reaction is carried out in an aprotic solvent. Suitable aprotic solvents include, but are not limited to, pyridine, dimethylformamide and tetrahydrofuran. The reaction mixture also contains a catalyst. Suitable catalysts include, but are not limited to, ester forming catalysts, such as 4-(N,N-dimethylamino)pyridine (DMAP). The reaction mixture is cooled with the aid of an ice bath to between −20 and 10° C. The reaction mixture is gradually warmed to room temperature and the reaction conditions generate a mixture of the mono-, bis-, tris- and tetraacylated products. The material may then be separated using chromatographic techniques such as silica gel chromatography to yield the desired bis-acylated product.

Attachment of the amino acid headgroup is accomplished using a N,N-dicyclohexylcarbodiimide (DCC) coupling protocol involving catalytic DMAP and pentafluorophenol. The resultant compounds of Formula I can be purified using chromatographic techniques, such as column chromatography.

The term amphiphilic lipid refers to a lipid having a hydrophobic portion which arranges into a hydrophobic phase and a hydrophilic portion which arranges toward the aqueous phase. Compounds of Formula I have both a hydrophobic portion and a hydrophilic portion. The portion of the molecule having R$^1$ and R$^2$ is the hydrophobic portion. The portion of the molecule possessing the quaternary ammonium salt is the hydrophilic or polar region.

The fatty acyl chains may be selected to be the same or different. They may be saturated or can have a single or multiple site(s) of unsaturation. In a preferred embodiment, R$^1$ and R$^2$ are C$_8$–C$_{20}$ alkyl. In a more preferred embodiment R$^1$ and R$^2$ are independently a myristyl, oleyl, lauryl, stearyl or a palmityl group.

The polar domain group can be derived from any α-amino acid moiety, requiring only that the α-amino acid contain a tertiary nitrogen. R$^3$ and R$^4$ are preferably the side chain of an α-amino acid. The term "side-chain" of an amino acid denotes the R group bonded to the α-carbon of a naturally-occurring amino acid, synthetic amino acid or an amino acid mimetic. This group includes, but is not limited to, hydrogen (glycine); methyl (alanine); isopropyl (valine); isobutyl (leucine); secbutyl (isoleucine); hydroxymethyl (serine); benzyl (phenylalanine); 3-indolemethyl (tryptophane) and the like.

In an alternative embodiment, R$^3$, Y$^1$ and the atoms to which they are bound, join to form an optionally substituted 5- or 6-membered heterocyclic ring. Suitable heterocyclic rings include, but are not limited to, pyrrolidine, imidazole, imidazolylmethyl, 4-hydroxypyrrolidine, piperidine, morpholine, pyridine, pyrazidine, pyrazole, pyrrole, and the like. In an alternative embodiment, $R^4$, $Y^6$, and the atoms to which they are bound, join to form an optionally substituted 5- or 6-membered heterocyclic ring. Suitable heterocyclic rings include, but are not limited to, pyrrolidine, imidazole, imidazolylmethyl, 4-hydroxypyrrolidine, piperidine, morpholine, pyridine, pyrazidine, pyrazole, pyrrole, and the like.

Additional structural diversity can be introduced into compounds of Formula I during the quaternization of the tertiary nitrogen to generate the ammonium salt polar domain. Suitable alkylation reagents include alkyl halides. Alkyl iodides are preferred.

The anion of the quaternary ammonium nitrogen may also be varied. Suitable anions include iodide, chloride, fluoride, bromide, oxyanions such as, carboxylates, sulfonates and sulfates. Iodide is preferred.

Compounds of Formula I which are preferred are dimyristoyl bis(N,N,N-trimethylglycyl) tetraester ammonium halogen salt and dioleoyl bis (N,N,N-trimethylglycyl) tetraester ammonium halogen salt.

B. Liposome Preparation and Composition

In a second aspect, this invention relates to a lipid-nucleic acid complex comprising a nucleic acid and at least one amphiphilic cationic lipid of Formula I. As indicated above, the methods of this invention involve complexing a cationic lipid with a nucleic acid. The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

The cationic lipid can be used alone, or in combination with a "helper" lipid. Preferred helper lipids are non-ionic or uncharged at physiological pH. Particularly preferred non-ionic lipids include, but are not limited to cholesterol and DOPE, with cholesterol being most preferred. The molar ratio of cationic lipid to helper can range from 2:1 to about 1:2, more preferably from about 1.5:1 to about 1:1.5 and most preferably is about 1:1.

In addition, the cationic lipids of this invention can be formulated into liposomes. Liposomes are constructed by well known techniques, such as described in *Liposome Technology*, Vols. 1–3 (G. Gregoriadis, Ed., CRC Press, 1993). Lipids are typically dissolved in chloroform and spread in a thin film over the surface of a tube or flask by rotary evaporation. If liposomes comprised of a mixture of lipids is desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires some minutes depending upon conditions, kind, and quality of the sonicator. Commonly, lipid concentrations are 1 mg/ml of aqueous phase, but could easily be higher or lower by a factor of ten.

The liposomes of the present invention comprise one or more of the cationic lipids of Formula I. Liposomes according to the invention optionally have one or more other amphiphiles. The exact composition of the liposomes will depend on the particular circumstances for which they are to be used. Those of ordinary skill in the art will find it a routine matter to determine a suitable composition. The liposomes of the present invention comprise at least one cationic lipid of the present invention. In a preferred embodiment, the liposomes of the present invention consist essentially of a single type of lipid of Formula I. In another preferred embodiment, the liposomes comprise mixtures of compounds of Formula I. In yet another preferred embodiment, the liposomes of the present invention comprise one or more lipids of Formula I in a mixture with one or more natural or synthetic lipids, e.g., cholesterol or DOPE.

In a preferred embodiment, mostly unilamellar liposomes are produced by the reverse phase evaporation method of Szoka & Papahadjopoulos, *Proc. Natl. Acad. Sci. USA*, 75: 4194–4198 (1978). Unilamellar vesicles are generally prepared by sonication or extrusion. Sonication is generally performed with a bath-type sonifier, such as a Branson tip sonifier at a controlled temperature as determined by the melting point of the lipid. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass.

Following liposome preparation, the liposomes that have not been sized during formation may be sized by extrusion to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high throughput basis if the liposomes have been sized down to about 0.2–0.4 microns.

Several techniques are available for sizing liposomes to a desired size. One sizing method is described in U.S. Pat. Nos. 4,529,561 or 4,737,323, herein incorporated by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10: 421–450 (1981). Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of about 0.05 microns to about 0.5 microns. More preferred are liposomes having a size of about 0.05 to 0.2 microns.

C. Nucleic Acid

Nucleic acids of all types may be associated with the cationic lipids and liposomes of the present invention and subsequently can be transfected. These include DNA, RNA, DNA/RNA hybrids (each of which may be single or double stranded), including oligonucleotides such as antisense oligonucleotides, chimeric DNA-RNA polymers, and ribozymes, as well as modified versions of these nucleic acids wherein the modification may be in the base, the sugar moiety, the phosphate linkage, or in any combination thereof.

From the foregoing it will be clear to those skilled in the art that the liposomes of the present invention are useful for both in vitro and in vivo application. The liposomes of the present invention will find use for nearly any in vitro application requiring transfection of nucleic acids into cells. For example, the process of recombinant production of a protein.

The nucleic acids may comprise an essential gene or fragment thereof, in which the target cell or cells is deficient in some manner. This can occur where the gene is lacking or where the gene is mutated resulting in under- or over-expression. The nucleic acids can also comprise antisense oligonucleotides. Such antisense oligonucleotides may be constructed to inhibit expression of a target gene. The foregoing are examples of nucleic acids that may be used with the present invention, and should not be construed to limit the invention in any way. Those skilled in the art will appreciate that other nucleic acids will be suitable for use in the present invention as well.

D. Method for Transfecting

In yet another aspect, this invention relates to a method for transfecting a nucleic acid into a cell. The method involves contacting a cell with a lipid-nucleic acid complex or aggregate comprising a nucleic acid and an amphiphilic cationic lipid of Formula I. Liposome-nucleic acid complex/aggregates may be prepared by adding an appropriate amount of nucleic acid to a liposome solution. For transfection, the weight ratio of cationic lipid to DNA is from slightly over 1:1 to perhaps 10:1. The amount of DNA can vary considerably, but is normally a few to a few tens of micrograms per standard culture dish of cells. Conditions may vary widely, and it is a routine matter and standard practice to optimize conditions for each type of cell, as suppliers of commercial materials recommend. Optimization involves varying the lipid to DNA ratio as well as the total amount of aggregate.

There is currently some uncertainty regarding the precise way in which nucleic acids and cationic lipids interact. In addition, the structure formed both before and during the transfection process is not definitively known. The present invention, however, is not limited by the particular structural type of complex formed by the liposomes and lipid aggregates of the present invention and the nucleic acids to be transfected. The phrase "liposome-nucleic acid aggregate" means any association of liposome or cationic lipid and nucleic acid that is capable of lipofection.

The lipid-nucleic acid aggregate is added to the cells, in culture medium, and left for some tens of minutes to several hours to perhaps overnight. Usually serum is omitted from the culture medium during this phase of transfection. Subsequently, the medium is replaced with normal, serum-containing medium and the cells are incubated for hours to days or possibly cultured indefinitely.

E. Specific Target Tissues

Specific targeting moieties can be used with the lipid:nucleic acid complexes of this invention to target specific cells or tissues. In one embodiment, the targeting moiety, such as an antibody or antibody fragment, is attached to a hydrophilic polymer and is combined with the lipid:nucleic acid complex after complex formation. Thus, the use of a targeting moiety in combination with a generic effector lipid:nucleic acid complex provides the ability to conveniently customize the complex for delivery to specific cells and tissues.

Examples of effectors in lipid:nucleic acid complexes include nucleic acids encoding cytotoxins (e.g., diphtheria toxin (DT), Pseudomonas exotoxin A (PE), pertussis toxin (PT), and the pertussis adenylate cyclase (CYA)), antisense nucleic acid, ribozymes, labeled nucleic acids, and nucleic acids encoding tumor suppressor genes such as p53, p110Rb, and p72. These effectors can be specifically targeted to cells such as cancer cells, immune cells (e.g., B and T cells), and other desired cellular targets with a targeting moiety. For example, as described above, many cancers are characterized by overexpression of cell surface markers such as HER2, which is expressed in breast cancer cells, or IL17R, which is expressed in gliomas. Targeting moieties such as anti-HER2 and anti-IL17R antibodies or antibody fragments are used to deliver the lipid:nucleic acid complex to the cell of choice. The effector molecule is thus delivered to the specific cell type, providing a useful and specific therapeutic treatment.

F. Drug Delivery

In still yet another aspect, this invention relates to a pharmaceutical composition or other drug delivery composition for administering a nucleic acid particle to a cell. This composition includes a lipid-nucleic acid complex comprising a nucleic acid and an amphiphilic cationic lipid of Formula I, and a pharmaceutically acceptable carrier therefor. As used herein, the term "pharmaceutical composition" means any association of a liposome or cationic lipid of Formula I and a nucleic acid and or a mixture of a conventional drug capable of be delivered into cells.

Cationic lipid-assisted drug delivery may be accomplished in the following manner. For drugs that are soluble in organic solvents, such as chloroform, the drug and cationic lipid are mixed in solvents in which both are soluble, and the solvent is then removed under vacuum. The lipid-drug residue is then dispersed in an appropriate aqueous solvent, which, in a preferred embodiment, is sterile physiological saline. The suspension then may optionally be subjected to up to several freeze/thaw cycles. It is then sonicated, either merely to reduce the coarseness of the dispersion or to reduce the particle size to 20–30 nm diameter, depending upon whether large or small particle size is most efficacious in the desired application. For some applications, it may be most effective to generate extruded liposomes by forming the suspension through a filter with pores of 100 nm diameter or smaller. For some applications, inclusion of cholesterol or natural phospholipids in the mixture used to generate the lipid-drug aggregate can be appropriate.

The liposome-drug aggregate may then be delivered in any suitable manner. For drugs that are soluble in aqueous solution and insoluble in organic solvents, the lipid mixture to be used for the lipid dispersion or liposomes is coated on the inside surface of a flask or tube by evaporating the solvent from a solution of the mixture. In general, for this method to be successful, the lipid mixture must be capable of forming vesicles having single or multiple lipid bilayer walls and encapsulating an aqueous core. The aqueous phase containing the dissolved drug, preferably a physiological saline solution, is added to the lipid, agitated to generate a suspension, and then optionally frozen and thawed up to several times.

To generate small liposomes the suspension is subjected to ultrasonic waves for a time necessary to reduce the liposomes to the desired average size. If large liposomes are desired, the suspension is merely agitated by hand or on a vortex mixer until a uniform dispersion is obtained, i.e., until visually observable large particles are absent. If the preparation is to have the drug contained only within the liposomes, then the drug in the aqueous phase is eliminated by dialysis or by passage through a gel-filtration chromatographic column (e.g., agarose) equilibrated with the aqueous phase containing all normal components except the drug. The lipid mixture used can contain cholesterol or natural lipids in addition to the cationic compounds of the present invention. The liposome-drug aggregate may then be delivered in any suitable manner.

G. Disease Treatment

In yet another aspect of the invention comprises novel methods of treating diseases arising from infection by a pathogen or from an endogenous DNA deficiency. These methods comprise administering a liposome-nucleic acid aggregate and/or liposome-drug aggregate solution to a mammal suffering from a pathogenic infection or DNA deficiency. If the disease is the result of infection by a pathogen, the nucleic acid can be an antisense oligonucleotide targeted against an DNA sequence in the pathogen that is essential for development, metabolism, or reproduction of the pathogen. If the disease is a DNA deficiency (i.e., wherein certain endogenous DNA is missing or has been mutated), resulting in under- or over-expression, the nucleic acid maybe the normal DNA sequence.

Several methods of in vivo lipofection have been reported. In the case of whole animals, the lipid-nucleic acid aggregate may be injected into the blood stream, directly into a tissue, into the peritoneum, instilled into the trachea, or converted to an aerosol, which the animal breathes. Zhu, et al., *Science* 261, 209–211 (1993) describe a single intravenous injection of 100 micrograms of a mixture of DNA and DOTMA:dioleoylphosphatidylethanaolamine that efficiently transfected virtually all tissues. It is also possible to use a catheter to implant liposome-DNA aggregates in a blood vessel wall, which can result in successful transformation of several cell types, including endothelial and vascular smooth muscle cells. Stribling, et al., *Proc. Natl. Acad. Sci. USA* 89, 11277–11281 (1992), demonstrated that aerosol delivery of a chloramphenicol acetyltransferase (CAT) expression plasmid complexed to cationic liposomes produced high-level, lung-specific CAT gene expression in mice in vivo for at least 21 days. They described the following procedure: Six milligrams of plasmid DNA and 12 mu mol of DOTMA/DOPE liposomes were each diluted to 8 mL with water and mixed; equal volumes were then placed into two Acorn I nebulizers (Marquest, Englewood, Colo.); animals were loaded into an Intox small-animal exposure chamber (Albuquerque) and an air flow rate of 4L/min was used to generate the aerosol (about 90 min were required to aerosolize this volume) the animals were removed from the chamber for 1–2 hours and the procedure was repeated. This protocol is representative of the aerosol delivery method.

The following Examples are presented for illustrative purposes only and are not intended, and should not be construed, to limit the invention in any manner.

EXAMPLES

Example 1

This example illustrates the synthesis of dimyristoyl-trimethylglycine pentaerythritol.

a.) Synthesis of the dimyristoyl diol

To a solution of pentaerythritol (1.0 g, 7.3 mmol) and DMAP (ca. 10 mg) in freshly distilled pyridine (75 mL) at 0° C. was added dropwise the myristoyl chloride (14.7 mmol). The resultant clear solution was gradually warmed to room temperature over 4 h and then transferred to a separatory funnel containing $CH_2Cl_2$ (200 mL). The organic solution was extracted with 10% HCl, the layers were separated, and the organic phase was dried over $Na_2SO_4$. The solvents were removed by rotary evaporation. The residue was purified using silica gel flash chromatography, eluting with a gradient of $CH_2Cl_2$ to 19:1 $CH_2Cl_2$:MeOH, to give the desired bisester product. The following is the analytical analysis. $R_f$=0.25, 19:1 MeOH:$CH_2Cl_2$; $^1$H NMR (300 MHz, $CDCl_3$) δ 4.14 (s, 4H, $CCH_2$O-acyl), 3.57 (s, 4H, $CCH_2$OH), 2.32 (t, J=7 Hz, 2H, —OC(O)$CH_2CH_2$—), 1.60 (m, 2H, —OC(O)$CH_2CH_2CH_2$—), 1.30 (m, 44H), 0.86 (t, J=7 Hz, 6H); $^{13}$C NMR (75 MHz, $CDCl_3$) δ 174.4, 62.4, 62.3, 44.8, 31.8, 30.0, 29.9–28.7, 24.9, 24.7, 22.6, 14.0; FTIR (KBr) 3298, 2917, 2850, 1732, 1468, 1179cm$^{-1}$; HRMS ($C_{33}H_{64}O_6$) calcd, 556.4703; found, 539.4679 [(M+H)$^+$—$H_2O$].

b.) Attachment and quaternization of the N,N-dimethylglycine headgroup.

To a suspension of N,N-dimethylglycine (140 mg, 1.35 mmol) and the diester from part "a" above (0.45 mmol) in DMF (6.8 mL) at room temperature was added pentafluorophenol (745 mg, 4.05 mmol). The mixture was warmed to 50° C. to effect complete dissolution of all solids. On cooling to room temperature, dicyclohexylcarbodiimide (300 mg, 1.45 mmol) and a catalytic amount of DMAP were added in one portion and stirred overnight. The reaction was diluted with $Et_2O$ and the precipitated urea was filtered. The filtrate was transferred to a separatory funnel and extracted successively with saturated $NH_4Cl$, water, and saturated $NaHCO_3$. The organic layer was dried over $Na_2SO_4$. The solvents were removed by rotary evaporation, and the residue was purified by column chromatography, eluting with a gradient of $CH_2Cl_2$ to 50:1 $CH_2Cl_2$:MeOH, to give the desired tetraesters. The analytical analysis for dimyristoyl bis(N,N-dimethylglycyl) tetraester is as follows: $R_f$=0.23, 9:1 $CH_2Cl_2$:MeOH; $^1$H NMR (300 MHz, $CDCl_3$) δ 4.17 (s, 4H, $(CH_3)_2NCH_2C(O)OCH_2$—) 4.11 (s, 4H, $CCH_2$O-acyl), 3.19 (s, 4H, $(CH_3)_2NCH_2C(O)O$—), 2.35 (s, 12H, $(CH_3)_2N$—), 2.30 (t, J=7 Hz, 4H, —OC(O)$CH_2CH_2$—), 1.57 (m, 4H, —OC(O)$CH_2CH_2CH_2$—), 1.25 (s, 48H), 0.86 (t, J=7 Hz, 6H); $^{13}$C NMR (75 MHz, $CDCl_3$) δ 174.4, 169.8, 62.4, 62.3, 56.2, 49.9, 44.9, 43.2, 34.8, 33.2, 32.1, 31.8, 29.9–28.5, 26.5, 25.5, 24.7, 22.5, 14.0; FTIR (KBr) 2922, 2853, 1746, 1467, 1284, 1148, 1064cm$^{-1}$; HRMS ($C_{41}H_{78}N_2O_8$) calcd, 726.5758; found, 727.5815 (M+H)$^+$.

The dimyristoyl bis(N,N-dimethylglycyl) tetraester from part "b" above was dissolved in excess iodomethane and the resulting solution was stirred at room temperature for 8 h. Iodomethane was removed under reduced pressure (Caution: a fume hood is required) to afford the corresponding crude bisiodide salt. Purification was accomplished by repeated recrystallization from acetonitrile. The analytical analysis of the quaternary ammonium iodide salt of dimyristoyl bis(N,N,N-trimethylglycyl) tetraester is as follows: $^1$H NMR (300 MHz, CDCl$_3$) δ 5.73 (s, 4H, (CH$_3$)$_3$NCH$_2$—), 4.32 (s, 4H, (CH$_3$)$_3$NCH$_2$C(O)OCH$_2$—), 4.18 (s, 4H, CCH$_2$O-acyl), 3.60 (s, 18H, (CH$_3$)$_3$N—), 2.30 (t, J=7 Hz, 4H, —OC(O)CH$_2$CH$_2$—), 1.60 (m, 4H, —OC(O)CH$_2$CH$_2$CH$_2$—), 1.25 (s, 48H), 0.86 (t, J=7 Hz, 6H); $^{13}$C NMR (75 MHz, CDCl$_3$) δ 172.4, 163.3, 65.2, 63.7, 61.2, 54.9, 49.9, 48.6, 47.7, 43.2, 34.6, 31.2, 29.8–28.9, 24.8, 22.8, 14.5; FTIR (KBr) 3011, 2917, 2850, 1743, 1472, 1247, 1191, 1123, 1021cm$^{-1}$; HRMS (C$_{43}$H$_{84}$N$_2$O$_8$I$_2$) calcd, 1010.4321; found, 883.5215 (M$^{2+}$+I$^-$).

In addition, using the same synthetic protocol as above, the dioleoyl bis(N,N,N-trimethylglycyl) tetraester was synthesized. The analytical data for that tetraester is as follows: $^1$H NMR (300 MHz, CDCl$_3$) δ 5.73 (s, 4H, (CH$_3$)$_3$NCH$_2$—), 5.34 (m, 4H), 4.33 (s, 4H, (CH$_3$)$_3$NCH$_2$C(O)OCH$_2$—), 4.18 (s, 4H, CCH$_2$O-acyl), 3.60 (s, 18H, (CH$_3$)$_3$N—), 2.31 (t, J=7 Hz, 4H, —OC(O)CH$_2$CH$_2$—), 1.60 (m, 4H, —OC(O)CH$_2$CH$_2$CH$_2$—), 1.27 (m, 40H), 0.86 (t, J=7 Hz, 6H); $^{13}$C NMR (75 MHz, CDCl$_3$) δ 172.7, 164.0, 129.8, 129.4, 65.2, 63.2, 61.3, 54.6, 42.3, 33.9, 31.7, 29.7, 29.5, 29.3, 29.1, 29.0, 27.0, 24.6, 22.4, 22.4, 13.8; FTIR (KBr) 3362, 3007, 2923, 2853, 1740, 1466, 1255, 1197, 1017cm$^{-1}$; HRMS (C$_{51}$H$_{96}$N$_2$O$_8$I$_2$) calcd, 1118.5260; found 991.6212 (M$^{2+}$+I$^-$).

Example 2

This example illustrates transfection of a plasmid DNA encoding the firefly luciferase gene.

a.) Liposome formulation.

The cationic lipid (1.0 mmol) and DOPE (1.0 mmol) were added as chloroform solutions to a 1.9 mL sample vial. The chloroform was evaporated using a stream of dry argon at room temperature. The resulting thin lipid films were placed under vacuum for 2–3 h to ensure that all traces of solvent were removed. Sterile water (1.0 mL) was then added to hydrate the lipid thin films, and the resultant suspension was vigorously mixed (vortex) at room temperature with occasional warming in a 60° C. water bath. The resultant 1.0 mM lipid suspension was used within 2 h of hydration.

b.) Cell culture.

NIH 3T3 cells were obtained from ATCC (CRL 1658) and grown in Dulbecco's Modified Eagle's Medium (DMEM; GIBCO) with 10% fetal calf serum (GIBCO) in a humidified 10% CO$_2$ incubator at 37° C. Human bronchial epithelial cells (16HBE14$_o$-) were cultured in Eagle's modified essential medium (MEM; GIBCO) supplemented with 10% fetal bovine serum (GIBCO), 1% glutamine (GIBCO), 1% penicillin and streptomycin (GIBCO), and grown in a 5% humidified CO$_2$ incubator at 37° C. Both cell lines were subcultured into sterile, untreated flasks.

c.) Transfection experiments.

The NIH 3T3 cells were plated at 50,000 cells per well on a standard 24 well plate (Corning, Corning, N.Y.) 24 h prior to transfection. Cells were approximately 80% confluent at the time of transfection. The HBE cells were plated at 50,000 cells/well on a 24 well tissue culture plate coated with fibronectin, vitrogen (collagen), and bovine serum albumin as previously described (Gruenert, D. C., Basbaum C. B., and Widdicombe J. H. (1990) *In Vitro Cell Dev Biol.,* 26, 411–418.) and were transfected as subconfluent monolayers 24 h prior to transfection. The growth media was removed via aspiration and each well was washed once with 0.5 mL buffered saline and overlaid with only MEM.

Cationic lipid-DNA complexes were prepared 15–40 mins prior to transfection. The pGL3-control vector encoding for firefly luciferase (Promega, Madison, Wis.) was slowly added to a diluted (DMEM or MEM) quantity of the cationic lipid:DOPE suspension in a polystyrene tube (Falcon #2058), and the lipid-DNA complex was diluted to a final volume of 800 mL. Typically (e.g. using DOTAP), 24 mL of the lipid suspension was used to complex 4.0 mg of the plasmid DNA, yielding a 2:1 cationic lipid:DNA phosphate molar ratio. Immediately on DNA addition, the suspension was vortexed and allowed to incubate for 15 min at room temperature. A 200 mL aliquot of the resultant lipid-DNA suspension was added to each well (1.0 mg DNA/well, n=4). The treated cells were then incubated for 4 h at 37° C. Control wells were treated with 200 mL of medium without supplement. At this time, 500 mL of the appropriate growth media including 10% FCS was added to all wells and the cells cultured for 48 h prior to lysis and analysis.

d.) Luciferase assay.

Relative luciferase activity was determined by using the Enhanced Luciferase Assay Kit and a Moonlight 2010 luminometer (Analytical Luminescence Laboratories, Sparks, Md.). Concentrated luciferase lysis buffer (233.3 mL) was applied to each well. Removal of growth media was not necessary prior to application of the lysis buffer. This technique enhances reproducibility by avoiding the possibility of cell loss during media removal. Luciferase light emissions from 31.1 mL of the lysate were measured over a 10 second period, and results were expressed as a function of assumed total lysate volume of 933.3 mL. Activity was expressed as relative light units, which are a function of assay conditions, luciferase concentration, luminometer photomultiplier tube sensitivity and background. Results are summarized in FIG. 1 as the mean (n=4) and standard deviation of total luciferase light units (RLU) obtained from cells lysed after transfection of 1.0 mg of DNA.

e.) Luciferase Transfection.

Many transfection lipids have shown improved activity on co-formulation with DOPE. To determine if the pentaerythritol lipids require this action, a DOPE titration using the dimyristoyl lipid DMTM(Gly) was conducted. The binary lipid mixtures were treated with pGL3-control, plasmid DNA encoding the firefly luciferase gene. NIH 3T3 transfection results from administration of the DMTM(Gly) lipoplexes are depicted in FIG. 1. The data reveals that an equimolar amount of DMTM(Gly) and DOPE affords near optimal transfection activity, with a larger percentage DOPE giving only negligible improvement. The results for DOTM(Gly):DOPE optimization were similar.

This example demonstrates that the pentaerythritol lipids DOTM(Gly) and DMTM(Gly) are capable of facilitating the intracellular delivery of plasmid DNA.

Example 3

This example illustrates cell cytotoxicity determined by evaluating lactate dehydrogenase activity.

a.) Cytotoxicity determination.

Cell viability was determined by evaluating the lactate dehydrogenase activity of post-transfected cells prior to lysis using the CellTiter 96 Aqueous Non-Radioactive Cell Proliferation Assay (Promega). The tetrazolium salt solution (Owen's Reagent; 100 mL) was added to each well and the 24 well plate was then gently agitated to ensure complete mixing. After incubation for an additional 3–4 h, each well was assayed for formazan production by removing an aliquot of the medium and diluting with 9 parts phosphate buffered saline (PBS) solution. The dilution was conducted in a 1.5 mL methylacrylate UV/VIS disposable cell, and the relative amount of formazan was determined by taking absorbance reading at 490 nm using PBS as the reference. The mean (n=4) of the absorbance values was calculated and compared to the mean absorbance value for non-transfected cells. The final results were expressed in terms of relative cytotoxicity. Relative cytotoxicity was calculated by subtracting from one the ratio of mean absorbance value for transfected cells over mean absorbance value for untreated cells. A relative cytotoxicity value of zero implies no difference from untreated cells, no measurable cytotoxicity. The maximum value of one implies total cell death for treated cells, no measurable formazan production indicating significant toxicity. Negative values may reflect enhanced formazan production as a consequence of cell growth relative to untreated cells.

b.) Cytotoxcity Assay.

To test whether (DMTM(Gly)) and (DOTM(GLY)) ameliorate lipid-induced cytotoxicity, a cell viability assay was performed. The relative cytotoxicity for these lipids and the popular transfection lipids DOTAP and DC-Chol was determined by measuring the lactate dehydrogenase activity for lipoplex-treated cells. The comparative assay was performed using NIH 3T3 and 16HBE14$_o$_ cells, and the results are plotted in FIGS. 2 and 3, respectively. A requisite for evaluation of cytotoxicity is the concurrent determination of relative transfection activity. Thus, the cationic lipids were evaluated for relative cytotoxicity immediately prior to determination of luciferase activity.

Figure 2:
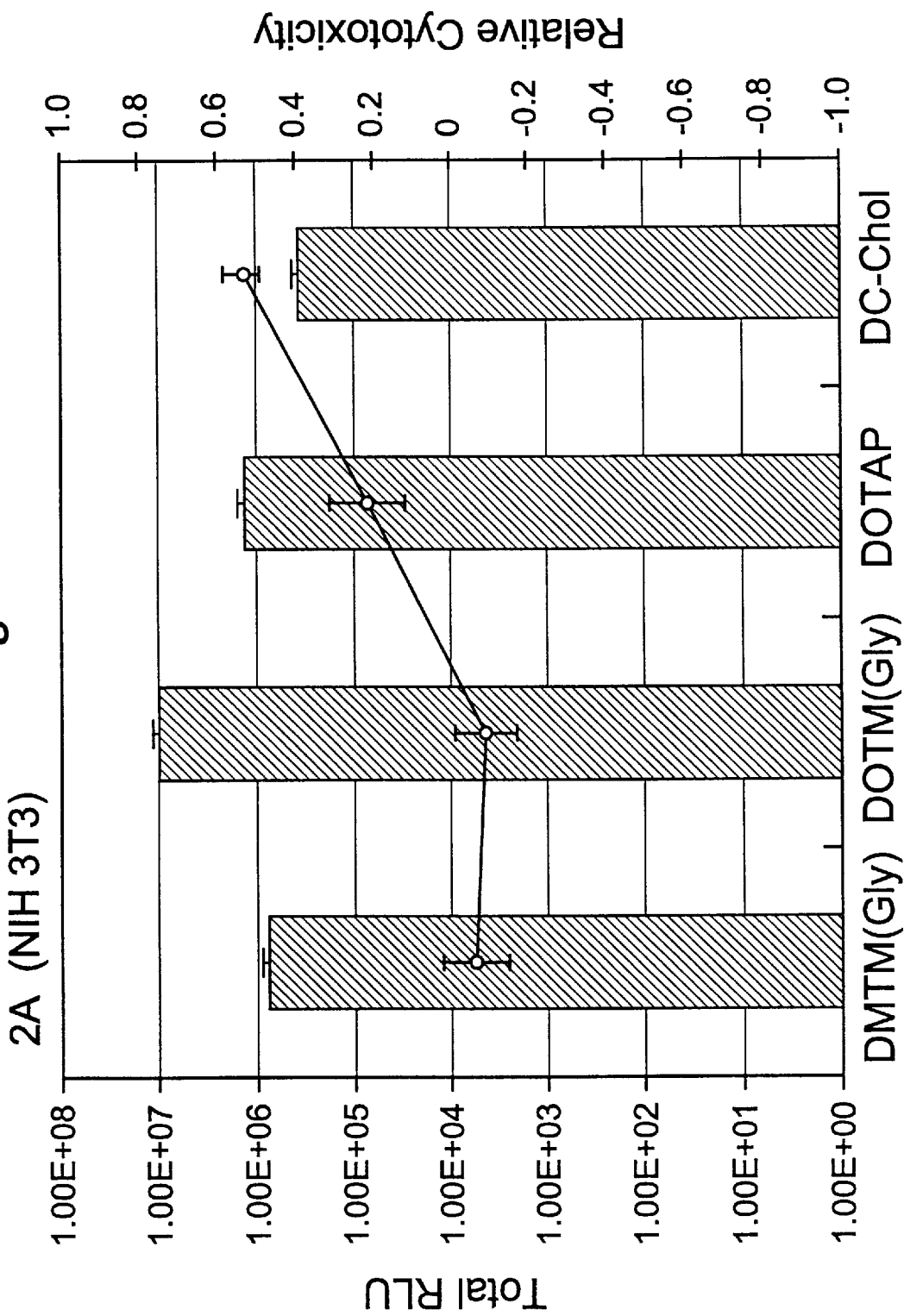
FIG. 2 is a bar graph showing luciferase transfection results as the mean (n=4) and standard deviation of total luciferase light units (RLU, left vertical axis) obtained from NIH 3T3 cells lysed after administration of 1 mg of DNA. Relative cytotoxicity, depicted by the solid line, is plotted according to the right vertical axis, calculated as described in Example 3. With the exception of DOTAP, 1:1 cationic lipid:DOPE liposomes at a 2:1 molar charge ratio (lipid charge to DNA phosphate charge) were used for lipoplex formation. DOTAP was used without a co-lipid.
Figure 3:
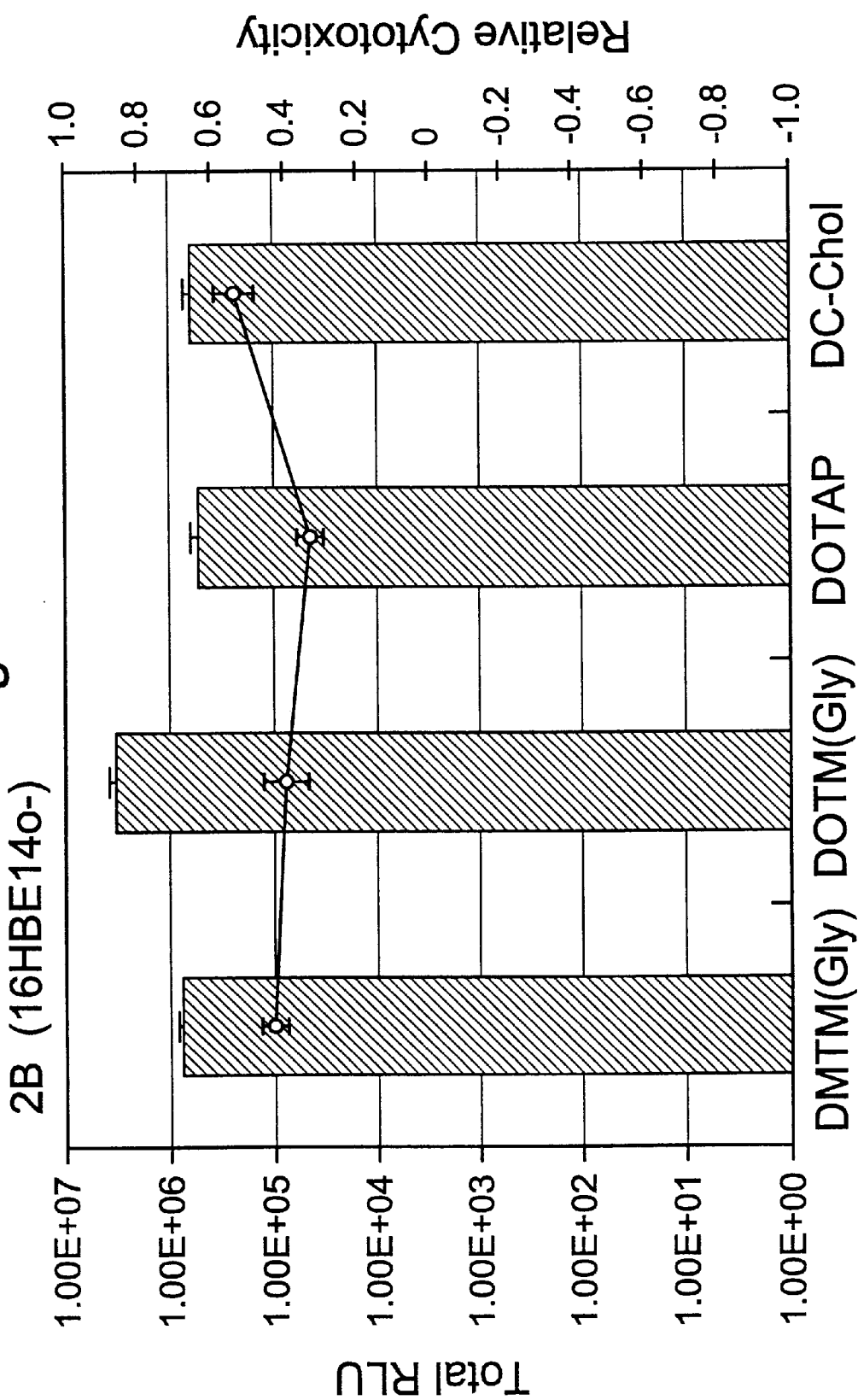
FIG. 3 is a bar graph showing luciferase transfection results as the mean (n=4) and standard deviation of total luciferase light units (RLU, left vertical axis) obtained from 16HBE14$_o-$ cells lysed after administration of 1 mg of DNA. Relative cytotoxicity, depicted by the solid line, is plotted according to the right vertical axis, calculated as described in Example 3. With the exception of DOTAP, 1:1 cationic lipid:DOPE liposomes at a 2:1 molar charge ratio (lipid charge to DNA phosphate charge) were used for lipoplex formation. DOTAP was used without a co-lipid.

FIGS. 2 and 3 show an overlay of transfection activity versus relative cytotoxicity for lipids DMTM(GLY) and DOTM(GLY), DOTAP and DC-Cholesterol. The dioleoyl analog DOTM(Gly) showed greater transfection activity than the dimyristoyl analog in both cell lines. DOTM(Gly) was also a more active transfection lipid in comparison to DOTAP and DC-Cholesterol, reaching an order of magnitude greater expression in both cell lines. The dimyristoyl lipid DMTM(Gly) exhibited transfection activities similar to DOTAP and DC-Chol.

The MTS assay, a widely used method to evaluate transfection associated cytotoxicity, measures mitochondrial lactate dehydrogenase activity through tetrazolium salt bioreduction. The MTS relative cytotoxicity data for the cationic lipid panel is illustrated in FIGS. 2 and 3. A reading of zero on the cytotoxicity scale (right vertical axis) indicates that the treated cells have comparable metabolic (dehydrogenase) activity relative to the untreated control cells, and implies the cationic lipid agent does not impair cellular function. The differences in relative cytotoxicity were most pronounced in the NIH 3T3 cells (FIG. 2). DMTM(Gly) and DOTM(Gly) did not induce a cytotoxic response whereas DC-Chol was found to be significantly more cytotoxic, impairing near 60% of the treated cells.

The low relative cytotoxicity responses determined for the pentaerythritol lipids in NIH 3T3 and HBE cell lines (FIG. 2) suggest that the use of intrinsically activated functional groups may be a useful strategy to reduce cationic-lipid induced toxicity.

Example 4

This example illustrates the transfection using the GFP reporter gene.

a.) Phase contrast and fluorescence microscopy.

Fluorescence experiments were conducted by transfecting the pEGFP-C1 C-Terminal protein fusion vector (Clontech, Palo Alto, Calif.) into NIH 3T3 and 16HBE14$_o$_ cells. The transfection protocol was identical to that of luciferase expression experiments in Example 1. Cells were grown for 48 h post-transfection, fixed with 3.7% formaldehyde, and viewed on a Zeiss ICM 405 inverted microscope with high resolution long-working distance objectives. Cells were photographed on the fluorescein channel and with phase contrast optics with a 40× water objective, using T-Max 400 (Kodak, Rochester, N.Y.) film.

b.) Green Fluorescent Protein (GFP) Transfection.

To probe relationships between cellular uptake, expression, and cytotoxicity, a transfection study was conducted using the GFP reporter gene. Fluorescent microscopy of cells treated with GFP-encoded plasmid is a sensitive tool for determining the occurrence of transgene expression. In agreement with the luciferase assay, DOTM(GLY) and DC-Chol of lipids were active in facilitating gene transfer as indicated by the presence of fluorescent cells. The phase contrast image for DOTM(Gly) showed normal cellular morphology, consistent with the low cytotoxicity response measured by the MTS assay. However, the phase contrast image for cells treated with DC-Chol showed dense regions of large vacuoles, indicative of cationic-lipid induced cytotoxicity. Cells treated with the cationic lipid formulations from the tested panel showed very similar morphology to cells transfected with their corresponding GFP-lipoplexes. HBE phase contrast pictures depicted some cellular debris and abnormal cellular morphology for all the cationic lipids examined, a result consistent with the MTS assay for cytotoxicity. Comparison of the fluorescent and phase contrast images revealed that the cationic lipid-induced cytotoxic response was not limited to those cells expressing GFP. Vacuolization was noted in cells that did and that did not express GFP. Thus, the onset of cytotoxicity precedes gene expression. Phase contrast images of cells transfected with DC-Chol depicted significantly greater vacuolization than cells transfected with DOTM(Gly), DOTAP, or DMTM (Gly).

Although the invention has been described with references to preferred embodiments and examples thereof, the scope of the present invention is not limited only to those described embodiments. As will apparent to persons skilled in the art, modifications and adaptations to the above-described invention can be made without departing from the spirit and scope of the invention, which is defined and circumscribed by the appended claims.

What is claimed is:

1. A compound having the formula

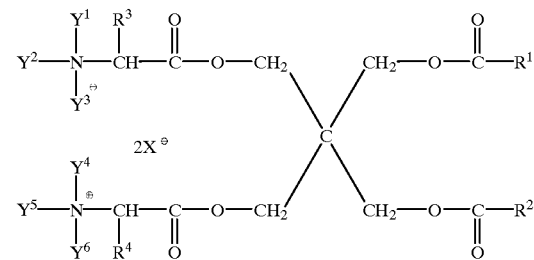

in which:

$R^1$ and $R^2$ are members independently selected from the group consisting of $C_8$–$C_{24}$ alkyl and $C_8$–$C_{24}$ alkenyl;

$R^3$ and $R^4$ are members independently selected from the group consisting of hydrogen, unsubstituted or substituted $C_1$–$C_8$ alkyl, unsubstituted or substituted arylalkyl, $C_1$–$C_8$ alkylthioalkyl, guanidinoalkyl, carboxyalkyl, aminoalkyl, carbamoyl $C_1$–$C_8$ alkyl and heteroarylalkyl;

$Y^1$, $Y^2$, $Y^3$, $Y^4$, $Y^5$, and $Y^6$ are independently members selected from the group consisting of hydrogen and $C_1$–$C_6$ alkyl;

X is a member selected from the group consisting of chloride, iodide, fluoride, bromide and an oxyanion;

or, $R^3$, $Y^1$ and the atoms to which they are bound, join to form an unsubstituted or substituted 5- or 6-membered heterocyclic ring; and $R^4$, $Y^6$ and the atoms to which they are bound join to form a 5- or 6-membered heterocyclic ring.

2. A compound in accordance with claim 1, in which:

$R^1$ and $R^2$ are members independently selected from the group consisting of $C_8$–$C_{20}$ alkyl and $C_8$–$C_{20}$ alkenyl;

$R^3$ and $R^4$ are members independently selected from the group consisting of hydrogen, methyl, ethyl, isopropyl, isobutyl, secbutyl, hydroxymethyl, thiomethyl, carboxymethyl, guanidinopropyl, carbamoylmethyl, carbamoylethyl, benzyl, p-hydroxyphenylmethyl, 1-hydroxyethyl, 2-(methylthio)ethyl, 3-indolemethyl, carboxyethyl and aminobutyl;

$Y^1$, $Y^2$, $Y^3$, $Y^4$, $Y^5$, and $Y^6$ are members independently selected from hydrogen, methyl, ethyl, propyl and butyl;

X is chloride or iodide;

or, $R^3$, $Y^1$ and the atoms to which they are bound, join to form a member selected from the group consisting of a pyrrolidine ring, a 4-hydroxypyrrolidine ring and an imidazolylmethyl ring; and $R^4$, $Y^6$ and the atoms to which they are bound, join to form a member selected from the group consisting of a pyrrolidine ring, a 4-hydroxypyrrolidine ring and an imidazolylmethyl ring.

3. A compound in accordance with claim 1, in which:

$R^1$ and $R^2$ are members independently selected from the group consisting of myristyl, oleyl, lauryl and palmityl;

$R^3$ and $R^4$ are members independently selected from the group consisting of ethyl and isopropyl;

$Y^1$, $Y^2$, $Y^3$, $Y^4$, $Y^5$, and $Y^6$ are members independently selected from the group consisting of hydrogen, methyl, ethyl and propyl; and X is iodide.

4. A compound in accordance with claim 1, in which:

$R^1$ and $R^2$ are both myristyl;

$R^3$ and $R^4$ are both hydrogen;

$Y^1$, $Y^2$, $Y^3$, $Y^4$, $Y^5$, and $Y^6$ are methyl; and

X is iodide.

5. A compound in accordance with claim 1, in which:

$R^1$ and $R^2$ are both oleyl;

$R^3$ and $R^4$ are both hydrogen;

$Y^1$, $Y^2$, $Y^3$, $Y^4$, $Y^5$, and $Y^6$ are all methyl; and

X is iodide.

6. A compound in accordance with claim 1, in which:

$R^1$ and $R^2$ are both myristyl;

$R^3$ and $R^4$ are both 3-indolemethyl;

$Y^1$, $Y^2$, $Y^3$, $Y^4$, $Y^5$, and $Y^6$ are all hydrogen; and

X is iodide.

* * * * *

UNITED STATES PATENT AND TRADEMARK OFFICE
CERTIFICATE OF CORRECTION

PATENT NO. : 6,043,390

DATED : March 28, 2000

INVENTOR(S) : Nantz, et al.

It is certified that error appears in the above-indentified patent and that said Letters Patent is hereby corrected as shown below:

column 16, line 50 please delete [+] and insert –⊕–.

column 16, line 54, please delete [+] and insert –⊕–.

Signed and Sealed this

Tenth Day of April, 2001

*Attest:*

NICHOLAS P. GODICI

*Attesting Officer*    Acting Director of the United States Patent and Trademark Office